(12) United States Patent
Sefkow et al.

(10) Patent No.: US 12,064,617 B2
(45) Date of Patent: Aug. 20, 2024

(54) MEDICAL LEADS WITH SEGMENTED ELECTRODES AND METHODS OF FABRICATION THEREOF

(71) Applicant: ADVANCED NEUROMODULATION SYSTEMS, INC., Plano, TX (US)

(72) Inventors: Ryan Sefkow, Frisco, TX (US); Christopher A. Crawford, Carrollton, TX (US); Jeffrey Mitchell, Little Elm, TX (US); Kevin Wilson, McKinney, TX (US); Raymond P. Bray, Dallas, TX (US); John R. Gonzalez, Frisco, TX (US)

(73) Assignee: ADVANCED NEUROMODULATION SYSTEMS, INC., Plano, TX (US)

( * ) Notice: Subject to any disclaimer, the term of this patent is extended or adjusted under 35 U.S.C. 154(b) by 627 days.

(21) Appl. No.: 17/317,935

(22) Filed: May 12, 2021

(65) Prior Publication Data
US 2021/0260367 A1 Aug. 26, 2021

Related U.S. Application Data

(60) Continuation of application No. 16/299,687, filed on Mar. 12, 2019, now Pat. No. 11,033,733, which is a
(Continued)

(51) Int. Cl.
*A61N 1/05* (2006.01)
*B29C 45/00* (2006.01)
(Continued)

(52) U.S. Cl.
CPC ........ *A61N 1/0534* (2013.01); *B29C 45/0055* (2013.01); *B29C 45/14311* (2013.01);
(Continued)

(58) Field of Classification Search
CPC .............. A61N 1/0534; B29C 45/0055; B29C 45/14311; B29C 45/14467;
(Continued)

(56) References Cited

U.S. PATENT DOCUMENTS

| 4,328,812 A | 5/1982 | Ufford et al. |
| 5,304,219 A | 4/1994 | Chernoff et al. |

(Continued)

*Primary Examiner* — Christopher A Flory
(74) *Attorney, Agent, or Firm* — Dean D. Small; The Small Patent Law Group, LLC

(57) ABSTRACT

In one embodiment, a method for fabricating a neurostimulation stimulation lead comprises: providing a plurality of ring components and hypotubes in a mold; placing an annular frame with multiple lumens over distal ends of the plurality of hypotubes to position a portion of each hypotube within a respective lumen of the annular frame; molding the plurality of ring components and the hypotubes to form a stimulation tip component for the stimulation lead, wherein the molding fills interstitial spaces between the plurality of ring components and hypotubes with insulative material; and forming segmented electrodes from the ring components after performing the molding.

17 Claims, 15 Drawing Sheets

Related U.S. Application Data continuation of application No. 15/163,012, filed on May 24, 2016, now Pat. No. 10,226,619, which is a division of application No. 14/541,795, filed on Nov. 14, 2014, now Pat. No. 9,370,653.

(60) Provisional application No. 61/912,517, filed on Dec. 5, 2013.

(51) Int. Cl.
  *B29C 45/14* (2006.01)
  *B29K 75/00* (2006.01)
  *B29L 31/00* (2006.01)

(52) U.S. Cl.
  CPC .. *B29C 45/14467* (2013.01); *B29C 45/14565* (2013.01); *B29C 45/14614* (2013.01); *B29C 2045/14524* (2013.01); *B29C 45/14639* (2013.01); *B29C 2793/009* (2013.01); *B29K 2075/00* (2013.01); *B29K 2995/0056* (2013.01); *B29L 2031/7546* (2013.01)

(58) Field of Classification Search
  CPC ........ B29C 45/14565; B29C 45/14614; B29C 45/14639; B29C 2045/14524; B29C 2793/009; B29K 2075/00; B29K 2995/0056; B29L 2031/7546

See application file for complete search history.

(56) References Cited

U.S. PATENT DOCUMENTS

| | | |
|---|---|---|
| 5,609,622 A | 3/1997 | Soukup et al. |
| 5,779,669 A | 7/1998 | Haissaguerre et al. |
| 5,807,395 A | 9/1998 | Mulier et al. |
| 6,249,708 B1 | 6/2001 | Nelson et al. |
| 6,363,286 B1 | 3/2002 | Zhu et al. |
| 6,480,747 B2 | 11/2002 | Schmidt |
| 6,889,092 B2 | 5/2005 | Zhu et al. |
| 7,168,605 B2 | 1/2007 | Walak |
| 7,422,585 B1 | 9/2008 | Eggers et al. |
| 8,460,286 B2 | 6/2013 | Stangenes et al. |
| 8,494,626 B2 | 7/2013 | Moffitt et al. |
| 8,825,151 B2 | 9/2014 | Gopinathan et al. |
| 9,370,653 B2 | 6/2016 | Sefkow et al. |
| 9,415,213 B2 * | 8/2016 | Venook ................ A61N 1/0551 |
| 10,137,226 B2 * | 11/2018 | Lafdi ................ A61M 25/0043 |
| 10,226,619 B2 | 3/2019 | Sefkow et al. |
| 2001/0016739 A1 | 8/2001 | Goldman et al. |
| 2001/0044646 A1 | 11/2001 | Marshall et al. |
| 2002/0058981 A1 | 5/2002 | Zhu et al. |
| 2002/0068930 A1 | 6/2002 | Tasto et al. |
| 2002/0095202 A1 | 7/2002 | Schmidt |
| 2003/0009095 A1 | 1/2003 | Skarda |
| 2004/0059277 A1 | 3/2004 | Maguire et al. |
| 2004/0138733 A1 | 7/2004 | Weber et al. |
| 2004/0243201 A1 | 12/2004 | Goldman et al. |
| 2004/0254621 A1 | 12/2004 | Jones et al. |
| 2005/0027235 A1 | 2/2005 | Knudsen et al. |
| 2006/0168805 A1 | 8/2006 | Hegland et al. |
| 2006/0195081 A1 | 8/2006 | Landis et al. |
| 2008/0039793 A1 | 2/2008 | Goldman et al. |
| 2008/0039829 A1 | 2/2008 | Goldman et al. |
| 2008/0140072 A1 | 6/2008 | Stangenes et al. |
| 2008/0249519 A1 | 10/2008 | Goldman et al. |
| 2009/0005775 A1 | 1/2009 | Jones et al. |
| 2010/0069983 A1 | 3/2010 | Peacock, III et al. |
| 2010/0137961 A1 | 6/2010 | Moffitt et al. |
| 2010/0269337 A1 * | 10/2010 | Dye ................ A61N 1/0531 29/874 |
| 2011/0071607 A1 | 3/2011 | Sethna et al. |
| 2011/0072659 A1 | 3/2011 | Swanson et al. |
| 2011/0077699 A1 | 3/2011 | Swanson et al. |
| 2011/0112531 A1 | 5/2011 | Landis et al. |
| 2011/0118815 A1 | 5/2011 | Kuzma et al. |
| 2011/0166518 A1 | 7/2011 | Nguyen et al. |
| 2011/0166519 A1 | 7/2011 | Nguyen et al. |
| 2013/0023972 A1 | 1/2013 | Kuzma et al. |
| 2013/0274844 A1 | 10/2013 | Leven et al. |
| 2013/0310823 A1 | 11/2013 | Gelfand et al. |
| 2014/0039513 A1 | 2/2014 | Hakala et al. |
| 2014/0052147 A1 | 2/2014 | Hakala et al. |
| 2014/0053401 A1 | 2/2014 | Kuzma et al. |
| 2014/0142398 A1 | 5/2014 | Patil et al. |
| 2014/0200438 A1 | 7/2014 | Millett et al. |
| 2014/0243809 A1 | 8/2014 | Gelfand et al. |
| 2015/0074997 A1 | 3/2015 | Kuzma et al. |
| 2015/0080995 A1 | 3/2015 | Seeley et al. |
| 2015/0157851 A1 | 6/2015 | Sefkow et al. |
| 2016/0263370 A1 | 9/2016 | Sefkow et al. |
| 2016/0324563 A1 | 11/2016 | Gelfand et al. |
| 2017/0291023 A1 | 10/2017 | Kuzma et al. |

\* cited by examiner

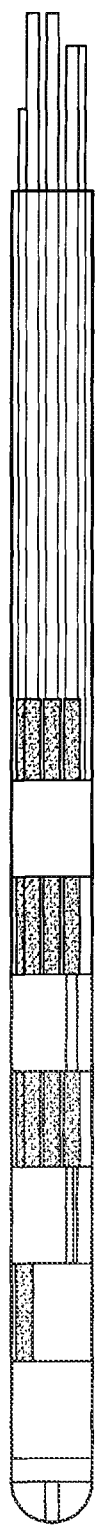
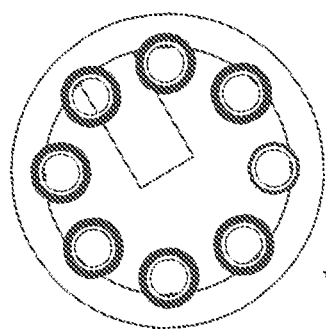
FIG. 1A
FIG. 1B

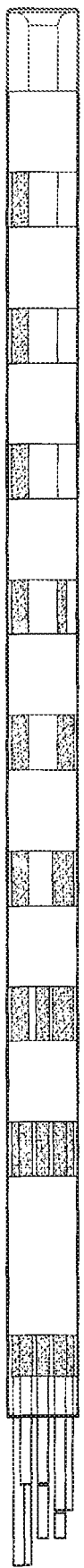
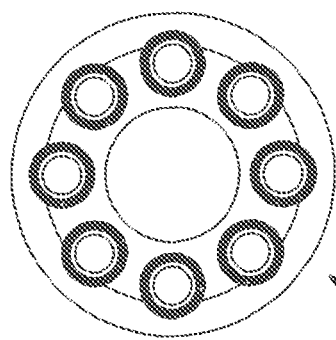
FIG. 2A
FIG. 2B

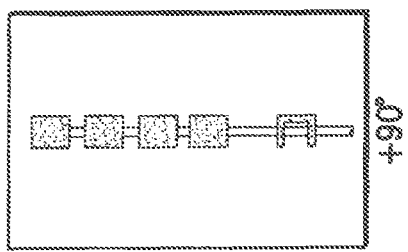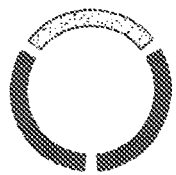
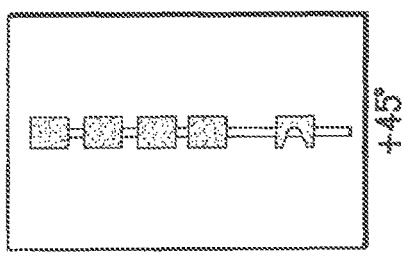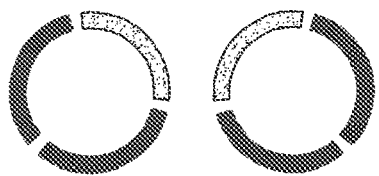
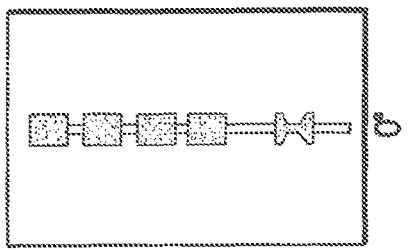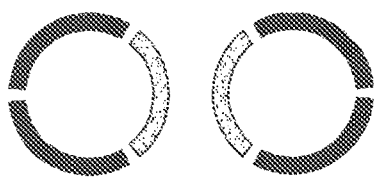
FIG. 11
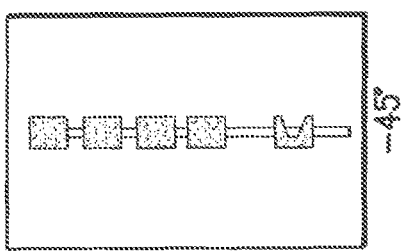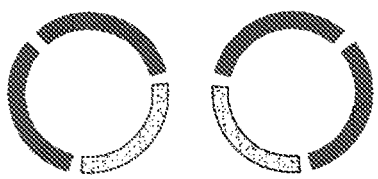
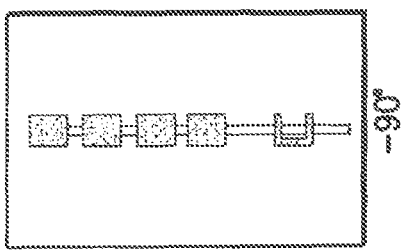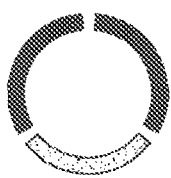

MEDICAL LEADS WITH SEGMENTED ELECTRODES AND METHODS OF FABRICATION THEREOF

RELATED APPLICATION

This application is a continuation of U.S. patent application Ser. No. 16/299,687, filed Mar. 12, 2019, which is a continuation of U.S. patent application Ser. No. 15/163,012, filed May 24, 2016, now U.S. Pat. No. 10,226,619, to issue on Mar. 12, 2019, which is a division of U.S. patent application Ser. No. 14/541,795, filed Nov. 14, 2014, now U.S. Pat. No. 9,370,653, which claims priority to U.S. Provisional Application Ser. No. 61/912,517, filed Dec. 5, 2013, which is incorporated herein by reference in their entirety.

TECHNICAL FIELD

This application is generally related to stimulation leads, and in particular to stimulation leads with segmented electrodes and methods of fabrication.

BACKGROUND INFORMATION

Deep brain stimulation (DBS) refers to the delivery of electrical pulses into one or several specific sites within the brain of a patient to treat various neurological disorders. For example, deep brain stimulation has been proposed as a clinical technique for treatment of chronic pain, essential tremor, Parkinson's disease (PD), dystonia, epilepsy, depression, obsessive-compulsive disorder, and other disorders.

A deep brain stimulation procedure typically involves first obtaining preoperative images of the patient's brain (e.g., using computer tomography (CT) or magnetic resonance imaging (MRI)). Using the preoperative images, the neurosurgeon can select a target region within the brain, an entry point on the patient's skull, and a desired trajectory between the entry point and the target region. In the operating room, the patient is immobilized and the patient's actual physical position is registered with a computer-controlled navigation system. The physician marks the entry point on the patient's skull and drills a burr hole at that location. Stereotactic instrumentation and trajectory guide devices are employed to control the trajectory and positioning of a lead during the surgical procedure in coordination with the navigation system.

Brain anatomy typically requires precise targeting of tissue for stimulation by deep brain stimulation systems. For example, deep brain stimulation for Parkinson's disease commonly targets tissue within or close to the subthalamic nucleus (STN). The STN is a relatively small structure with diverse functions. Stimulation of undesired portions of the STN or immediately surrounding tissue can result in undesired side effects. Mood and behavior dysregulation and other psychiatric effects have been reported from stimulation of the STN in Parkinson's patients.

To avoid undesired side effects in deep brain stimulation, neurologists often attempt to identify a particular electrode for stimulation that only stimulates the neural tissue associated with the symptoms of the underlying disorder while avoiding use of electrodes that stimulate other tissue. Also, neurologists may attempt to control the pulse amplitude, pulse width, and pulse frequency to limit the stimulation field to the desired tissue while avoiding other tissue.

As an improvement over conventional deep brain stimulation leads, leads with segmented electrodes have been proposed. Conventional deep brain stimulation leads include electrodes that fully circumscribe the lead body. Leads with segmented electrodes include electrodes on the lead body that only span a limited angular range of the lead body. The term "segmented electrode" is distinguishable from the term "ring electrode." As used herein, the term "segmented electrode" refers to an electrode of a group of electrodes that are positioned at approximately the same longitudinal location along the longitudinal axis of a lead and that are angularly positioned about the longitudinal axis so they do not overlap and are electrically isolated from one another. For example, at a given position longitudinally along the lead body, three electrodes can be provided with each electrode covering respective segments of less than 120° about the outer diameter of the lead body. By selecting between such electrodes, the electrical field generated by stimulation pulses can be more precisely controlled and, hence, stimulation of undesired tissue can be more easily avoided.

Implementation of segmented electrodes are difficult due to the size of deep brain stimulation leads. Specifically, the outer diameter of deep brain stimulation leads can be approximately 0.06 inches or less. Fabricating electrodes to occupy a fraction of the outside diameter of the lead body and securing the electrodes to the lead body can be quite challenging.

SUMMARY

In some embodiments, a method for fabricating a neurostimulation stimulation lead comprises: providing a plurality of ring components and hypotubes in a mold; molding the plurality of ring components and the hypotubes to form a stimulation tip component for the stimulation lead; and forming segmented electrodes from the ring components after performing the molding. The hypotubes may be welded to the electrodes before placement within a mold for an injection molding process. According to any of the discussed embodiments, the method further comprises applying a first weld and a second weld to attach each hypotube to a corresponding ring component. The molding process fills the interstitial spaces with suitable insulative material.

According to any of the discussed embodiments, the neurostimulation lead is adapted for long term implant within a patient. In one embodiment, the neurostimulation lead is a deep brain stimulation lead. The neurostimulation lead may comprise a suitable configuration of segmented electrodes (four rows of two segmented electrodes, two rows of four segmented electrodes, or two rows of three segmented electrodes with two conventional ring electrodes as example configurations). According to any of the discussed embodiments, the neurostimulation lead may comprise a non-symmetric hour-glass radial marker.

According to any of the discussed embodiments, the method further comprises: providing a pre-molded frame component with multiple lumens about the plurality of hypotubes, wherein the frame is placed about the plurality of hypotubes before the molding process is performed to retain the plurality of hypotubes at respective angular positions during the molding process. The re-molding frame structure is integrated within the stimulation tip component by the molding process. The pre-molded frame may be fabricated using a suitable biocompatible polymer material. According to any of the discussed embodiments, the stimulation tip components may employ a relatively stiff polymer material (e.g., shore 75D) while polymer material of the lead body is relatively less stiff (e.g., shore 55D).

According to any of the discussed embodiments, the plurality of hypotubes comprise different lengths for multiples ones or all of the plurality of hypotubes. The hypotubes extend from the molded portion of the stimulation or terminal tip by respective lengths. The different lengths facilitate subsequent connection of the hypotubes to conductor wires of a lead body in a correct order.

According to any of the discussed embodiments, an insulative coating is disposed on each hypotube of the plurality of hypotubes. The insulative coating may be a parylene material (one or more respective polyxylylene polymers). Weld operations may be performed on the coated hypotubes to mechanically and electrically connect the hypotubes to various other components of the neurostimulation lead. For example, the conductor wires of a lead body of the neurostimulation lead may be welded to the coated hypotubes.

According to any of the discussed embodiments, the method further comprises providing insulative material over an exposed portion of the plurality hypotubes after connection to conductor wires of a lead body and reflowing the insulative material to enclose the previously exposed portion of the plurality of hypotubes and to integrate a stimulation and/or connector tip component with the lead body. The insulative material may be provided in a "clam-shell" form to facilitate wrapping around the connection region between the stimulation or terminal tip and the lead body. The insulative material may be a suitable reflowable polymer material.

According to any of the discussed embodiments, each ring component may comprise a step-down region. The step-down region is secured underneath the surface of the neurostimulation lead formed by the insulative material provided during the molding process. The roughness of the surface of step-down region may be increased by bead-blasting to facilitate bonding or adhesion to the insulative material provided during the molding process. Also, the inner surface of the ring components may be similarly processed to facilitate adhesion to the insulative material provided during the molding process.

According to any of the discussed embodiments, the hypotubes are connected to wires of a lead body of the neurostimulation lead. The method further comprises twisting the lead body from a first configuration with linearly arranged conductor wires to obtain a second configuration with helically arranged conductor wires. The method further comprises heating the lead body to retain the helical arrangement of conductor wires in the finished neurostimulation lead. The twisting may be performed before or after connection to the hypotubes.

In some embodiments, a neurostimulation lead is fabricated using any of the methods discussed herein. In some embodiments, a neurostimulation system includes an implantable pulse generator (IPG) and one or more neurostimulation leads fabricated using any of the methods discussed herein.

The foregoing and other aspects, features, details, utilities and advantages of the present disclosure will be apparent from reading the following description and claims, and from reviewing the accompanying drawings.

BRIEF DESCRIPTION OF THE DRAWINGS

FIGS. 1A and 1B depict a stimulation tip component shown in respective views according to some representative embodiments.

FIGS. 2A and 2B depict a terminal end component according to respective views according to some representative embodiments.

FIG. 11 depicts the orientation of a lead with segmented electrodes and an orientation marker according to one representative embodiment matched against corresponding images of the lead.

DETAILED DESCRIPTION

The present application is generally related to a process for fabricating a stimulation lead comprising multiple segmented electrodes. In one preferred embodiment, the lead is adapted for deep brain stimulation (DBS). In other embodiments, the lead may be employed for any suitable therapy including spinal cord stimulation (SCS), peripheral nerve stimulation, peripheral nerve field stimulation, dorsal root or dorsal root ganglion stimulation, cortical stimulation, cardiac therapies, ablation therapies, etc.

In some representative embodiments, multiple components are fabricated and assembled to form a stimulation lead including segmented electrodes. Referring to FIGS. 1A and 1B, stimulation end component 100 is shown in respective views. In one embodiment, stimulation end component 100 is fabricated by molding the respective components using a suitable biocompatible polymer to form an integrated assembly. In one embodiment, injection molding is the process selected for fabrication of stimulation end component 100, although any suitable molding technique may be employed. The various components include a plurality of electrodes and hypotubes. The electrodes are connected to a plurality of hypotubes. The stimulation end component 100 may also include a radio-opaque marker to permit the orientation of the lead to be determined post-implant using suitable medical imaging. Stimulation end component 100 preferably includes a plurality of segmented electrodes. In one embodiment, a distal ring electrode, two rows of three segmented electrodes, and a proximal ring electrode are provided, although any suitable electrode configuration may be selected. One other possible electrode configuration includes two rows of four segmented electrodes. Another possible electrode configuration includes four rows of two segmented electrodes.

FIGS. 2A and 2B depict terminal end 200 according to respective views. Terminal end component 200 may be fabricated in a substantially similar manner to stimulation end component 100 using suitable molding techniques. Terminal end component 200 may preferably comprise ring contacts for placement within the header of an implantable pulse generator (IPG). Terminal end component 200 may also comprise a non-active contact ring for use with a set screw and/or contact with an initial seal element within the header of the IPG. Terminal end component 200 preferably comprises a stylet guide and central lumen for the stylet.

Figure 3A:
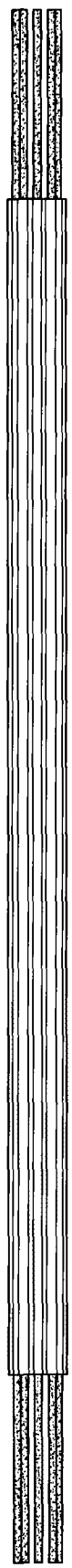
FIGS. 3A-3C depict a lead body component according to some representative embodiments.
Figure 3B:
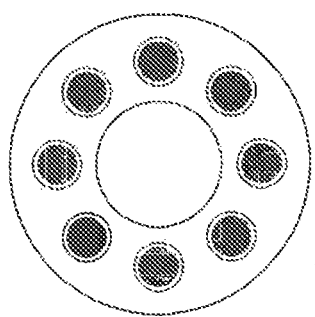
Figure 3C:
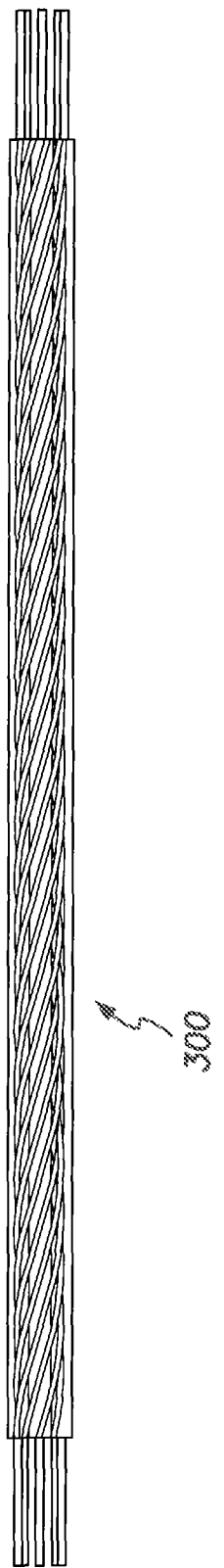

FIGS. 3A and 3B depict lead body component 300. In one embodiment, a multi-lumen component of insulative material is initially molded or otherwise suitably fabricated. Conductors are placed within the various lumens as shown in FIGS. 3A and 3B. The conductors may extend from the distal and proximal ends of the body of insulative material. A central lumen is also provided in lead body component 300 for use of the finished stimulation lead with a stylet. In some embodiments, after placement of the conductor wires, lead body component 300 is twisted one or more times and subjected to heating (as shown in FIG. 3C). By heat setting a twist configuration to the lead body component 300, transfer of bending at one end of lead body component 300 to the other end of lead body component 300 is prevented. Preventing bend and other deformation transfers from occurring may be helpful during handling of the finished lead during an implant procedure.

Figure 4A:
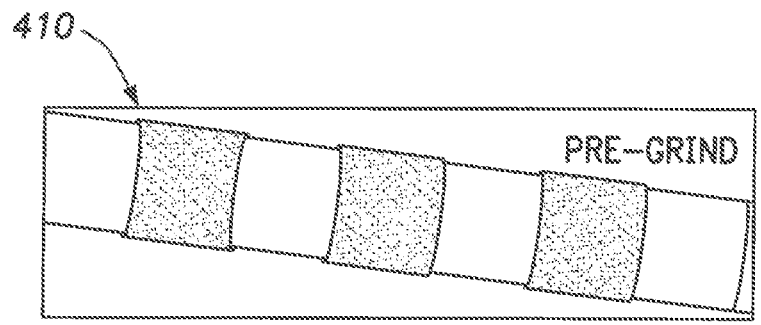
FIGS. 4A-4F depict respective components of a stimulation tip component according to some representative embodiments.
Figure 4B:
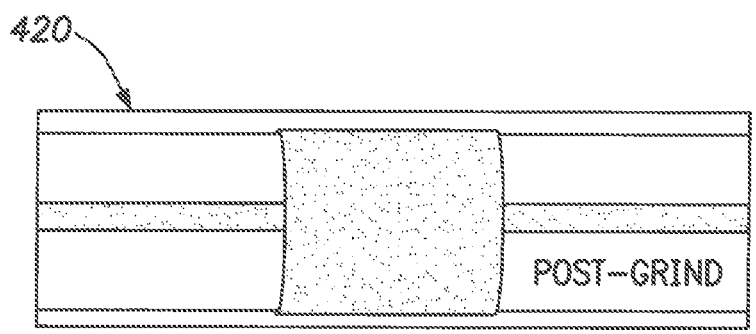
Figure 4C:
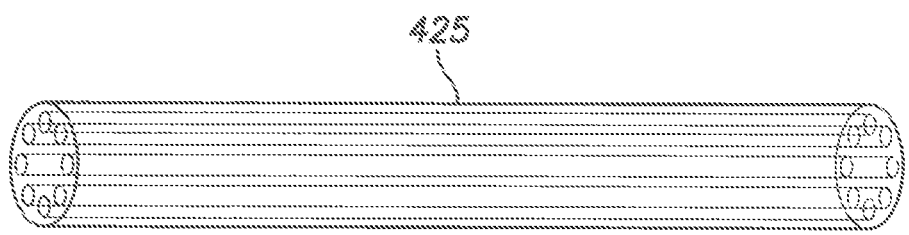
Figure 4D:
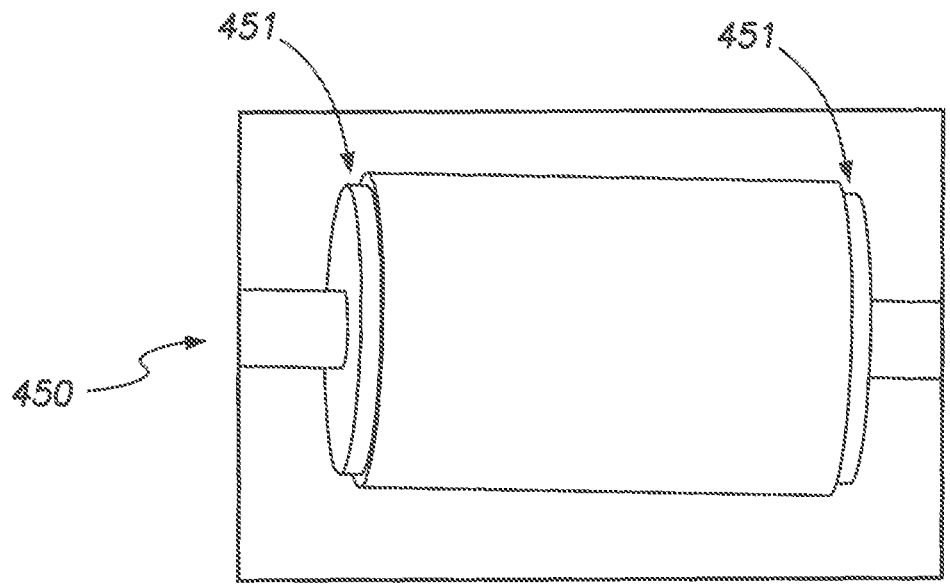
Figure 4F:
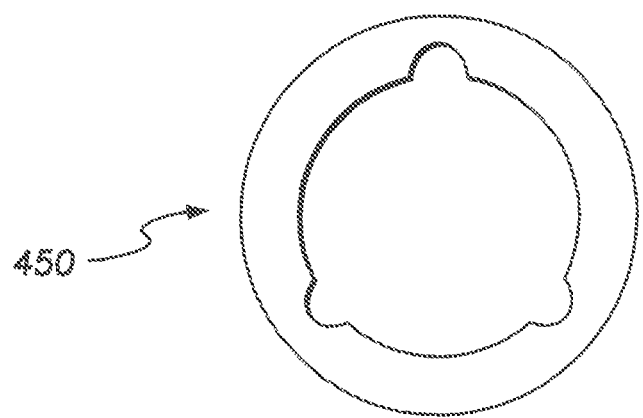

FIGS. 4A-4D depict components of stimulation end component 100 according to some embodiments. In FIG. 4D, ring component 450 is shown. Ring component 450 is a substantially annular structure of suitable conductive material. Ring component 450 includes one or more step-down regions 451 where the outer diameter is reduced. The step-down regions may permit ring component 450 to be more securely integrated within the body of the stimulation end component 100 in the molding process. That is, the step-down regions 451 may be disposed below the outer surface of the insulative material after molding occurs. Also, step-down regions 450 may be bead blasted to increase the roughness of the surface of the electrodes to improve bonding or adhesion to the insulative material. Also, the inner diameter (not shown) of ring component 450 may be similar processed. Other techniques for application of abrasive materials to roughen the respective surfaces may be alternatively applied. The increase in surface roughness may further secure the integration of the metal components with the insulative material provided during the molding process. Additionally, ring component 450 may comprise longitudinal grooves or cuts (shown in FIG. 4F) along the inner diameter of component 450 to facilitate separation of the component 450 into multiple segmented electrodes by a grinding process or other suitable processing. The reduced wall thickness along such grooves permits separation during grinding operations as detailed in U.S. patent Ser. No. 12/873,838, filed Sep. 1, 2010 (published as U.S. Patent Pub. No. 2011/0047795) which is incorporated herein by reference.

Figure 4E:
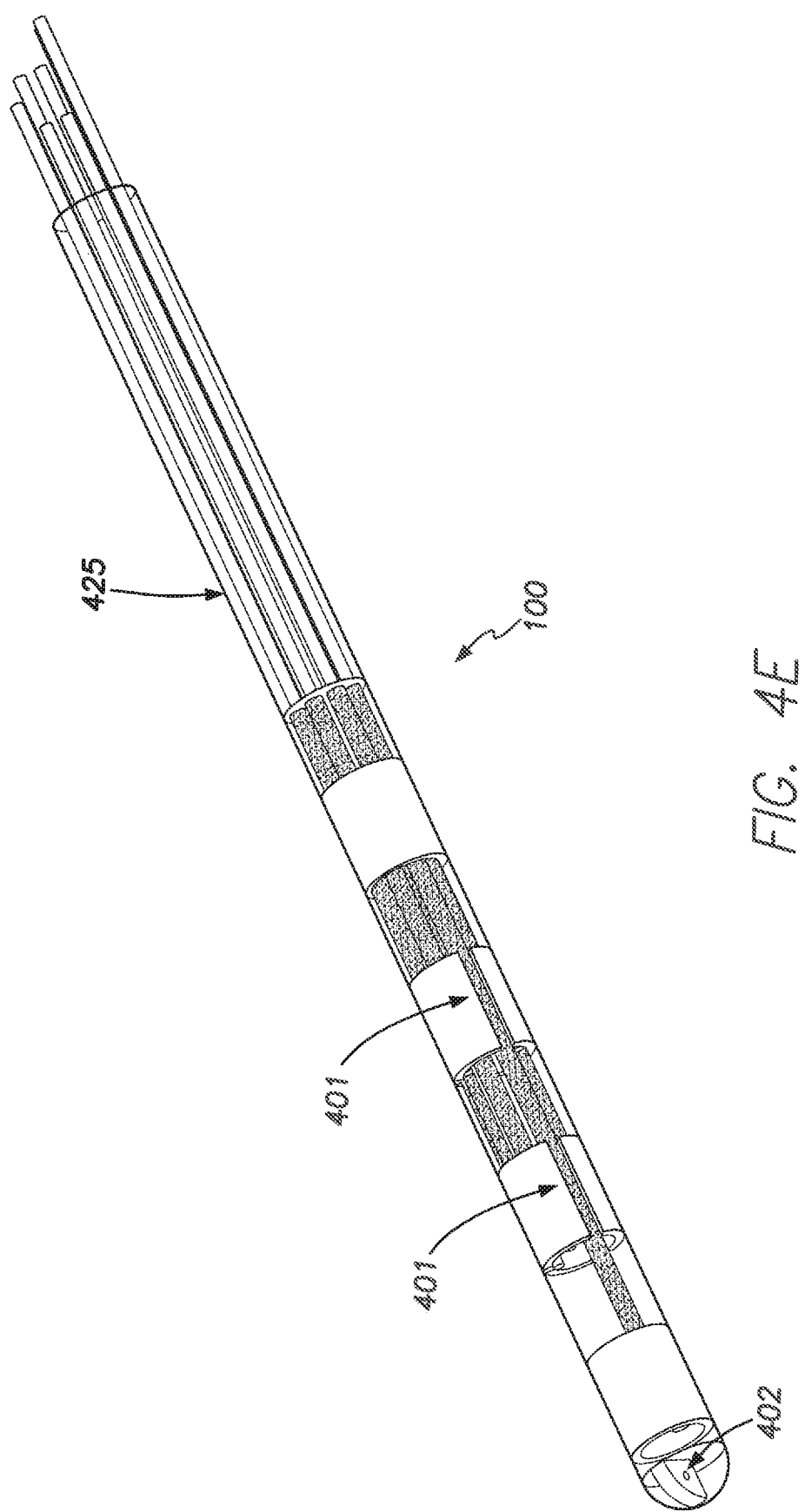

FIG. 4A depicts component 410 which includes the ring components 450 (before grinding operations), ring electrodes, and the hypotubes integrated using molded insulative material. Component 410 is subjected to suitable grinding operations to provide stimulation tip component 420 in which the grinding produces the segmented electrodes from ring components 450. Pre-molded frame 425 (shown individually in FIG. 4C) is placed over a portion of the hypotubes as shown in FIG. 4E to form stimulation end component 100. Frame 425 may provide stability to hypotubes within the interior of the finished stimulation lead and prevent hypotubes from migrating to the outer surface of the stimulation lead. Also, frame 425 may ensure that hypotubes are maintained in a regular angular pattern to facilitate connection with other portions of the stimulation lead. A portion of hypotubes may preferably remain exposed to facilitate subsequent lead fabrication operations. Also, the lengths of the hypotubes may be preferably staggered as shown in FIG. 4E. The difference in length of the respective hypotubes permits ready identification of the connection of a specific hypotube to a corresponding electrode to facilitate further integration operations for fabrication of the stimulation lead.

Figure 5:
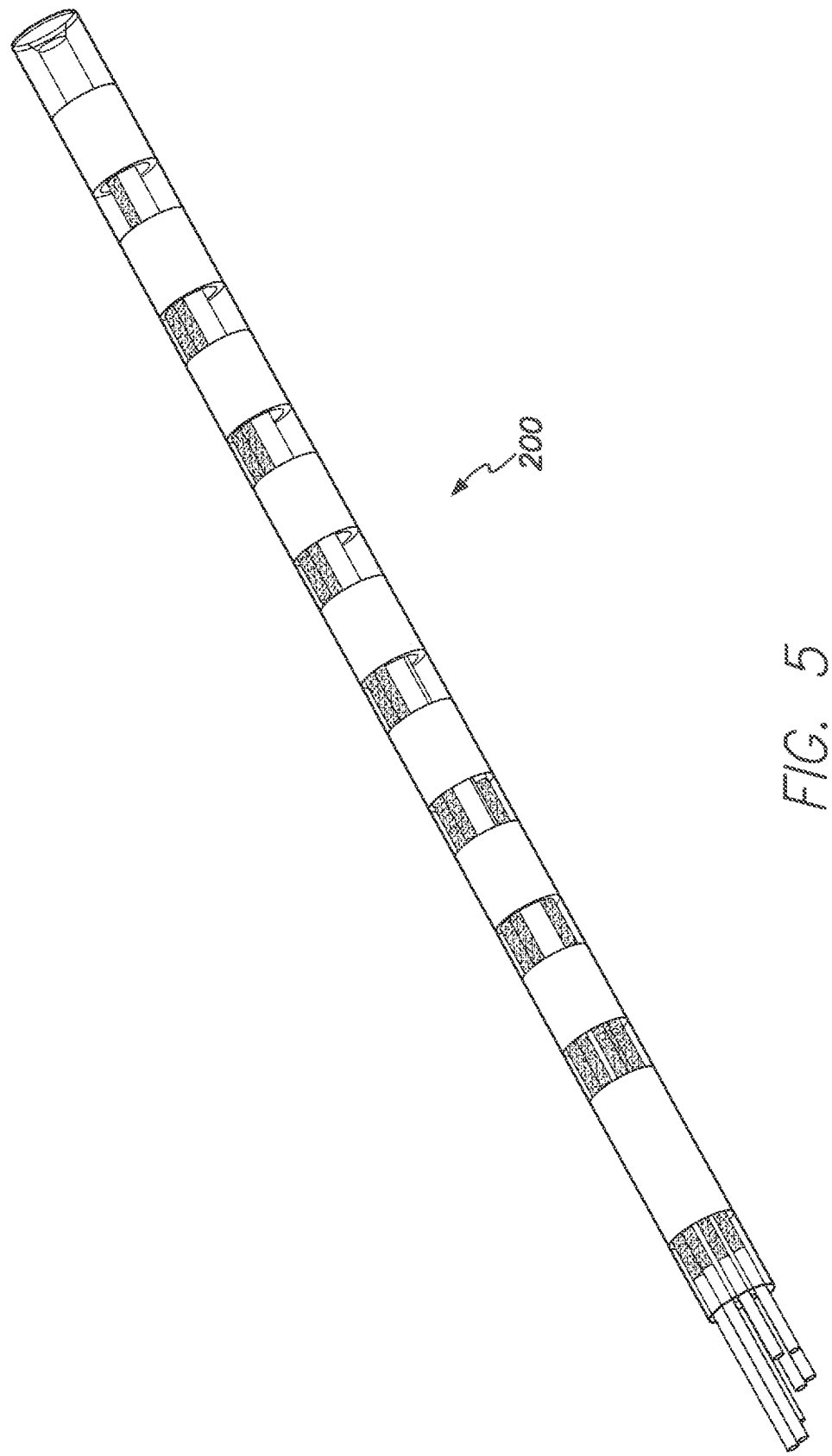
FIG. 5 depicts an additional view of a terminal end component according to some representative embodiments.

FIG. 5 depicts an additional view of terminal end component 500. As discussed previously, terminal end component 500 may be fabricated in substantially the same manner as stimulation end component 100. Terminal end component 500 may include a hypotube configuration (i.e., varied lengths of hypotubes) that mirrors the arrangement of hypotubes on stimulation end component 100 to facilitate the lead fabrication process. Terminal end component 500 may include a suitable frame component surrounding the hypotubes. Further, terminal end component 500 may include an additional contact which is not connected to a hypotube. The additional contact may be employed for use with a set-screw in the header of an extension and/or IPG.

Figure 6:
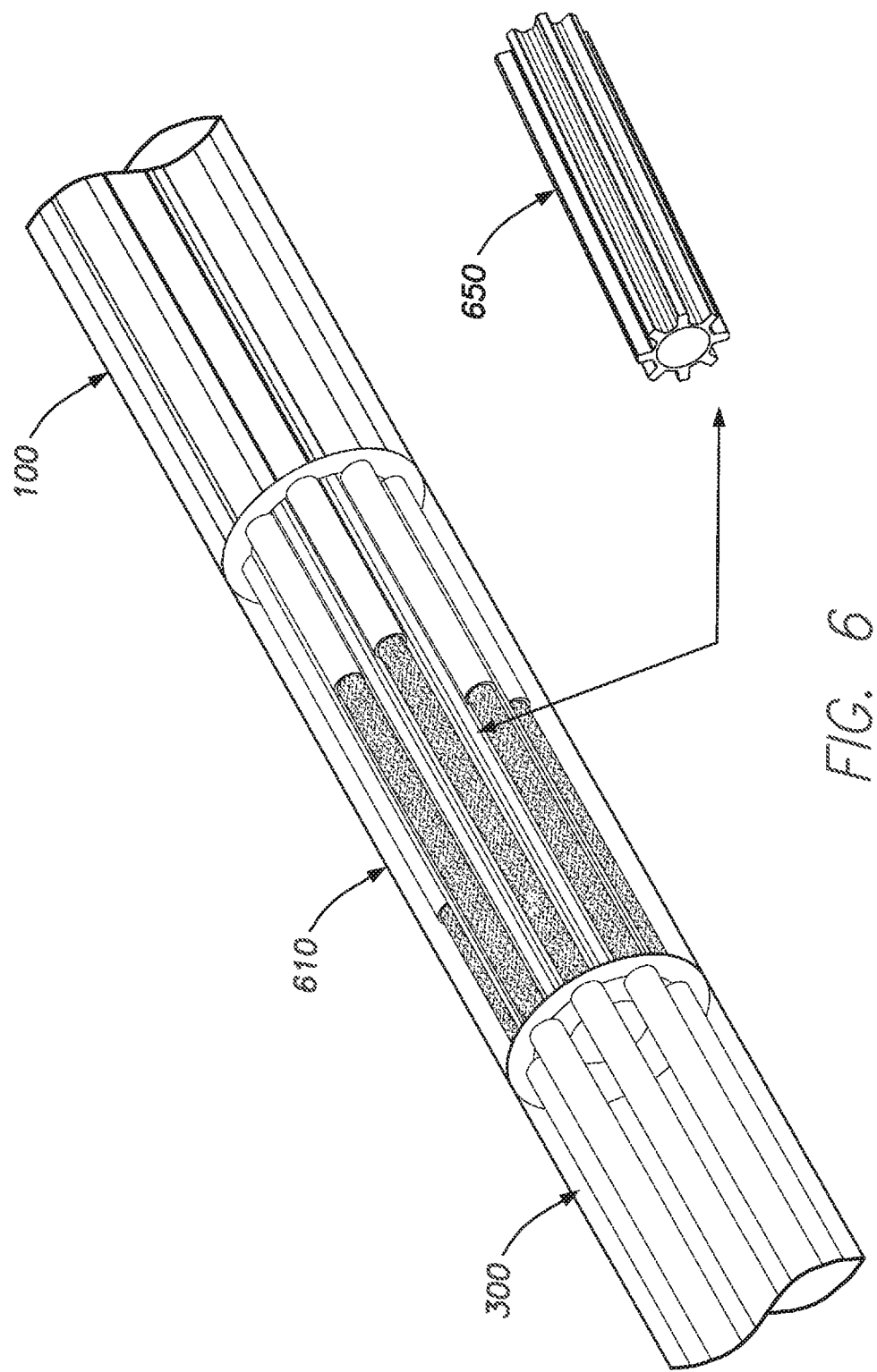
FIG. 6 depicts integration of a stimulation tip component with a lead body component according to some representative embodiments.

FIG. 6 depicts integration of stimulation end component 100 with lead body component 300. Lead body component 300 is placed next to "gear" component 650. Gear component 650 may be fabricated from suitable biocompatible material such as PEEK or ETFE. Gear component 500 comprises a plurality of grooves or channels for the conductors of lead body component 300 and the hypotubes of stimulation end component 100. The conductors of lead body component 300 are placed within the hypotubes and suitable welding operations are performed (e.g., laser welding). Clamshell component 610 is preferably placed over the exposed connection region of conductors and hypotubes. Clamshell component 610 is preferably fabricated from a reflowable (e.g., a biocompatible polyurethane or thermoplastic polycarbonate urethane) insulative material. The material of component 610 is selected to possess a lower flow temperature than of gear component 650. When reflow operations occur, gear component 650 retains the hypotubes and/or conductors in place and prevents mutual contact between such conductive material. Thereby, shorting between such components is prevented.

Similar operations may occur to connect the other end of lead body component 300 to terminal end component 200 to form the stimulation lead.

Figure 7:
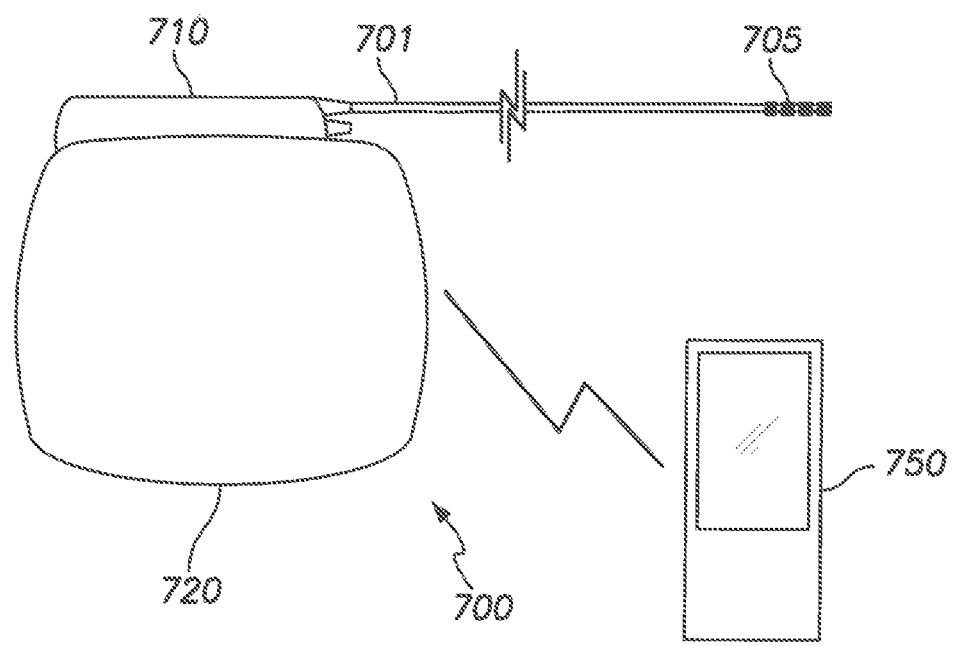
FIG. 7 depicts a finished stimulation lead within a neurostimulation or other active medical device system according to some embodiments.

FIG. 7 depicts a finished stimulation lead within a neurostimulation or other active medical device system according to some embodiments. Neurostimulation system 700 includes pulse generator 720 and one or more stimulation leads 701. Examples of commercially available pulse generator include the EON™, EON MINI™, LIBRA™, and BRIO™ pulse generators available from St. Jude Medical, Inc. Other active medical devices could be employed such as pacemakers, implantable cardioverter defibrillator, gastric stimulators, functional motor stimulators, etc. Pulse generator 720 is typically implemented using a metallic housing that encloses circuitry for generating the electrical pulses for application to neural tissue of the patient. Control circuitry, communication circuitry, and a rechargeable battery (not shown) are also typically included within pulse generator 720. Pulse generator 720 is usually implanted within a subcutaneous pocket created under the skin by a physician.

As fabricated according to techniques described herein, lead 701 is electrically coupled to the circuitry within pulse generator 720 using header 710. Lead 701 includes terminals (not shown) that are adapted to electrically connect with electrical connectors (e.g., "Bal-Seal" connectors which are commercially available and widely known) disposed within header 710. The terminals are electrically coupled to conductors (not shown) within the lead body of lead 701. The conductors conduct pulses from the proximal end to the distal end of lead 701. The conductors are also electrically coupled to electrodes 705 to apply the pulses to tissue of the patient. Lead 701 can be utilized for any suitable stimulation therapy. For example, the distal end of lead 701 may be implanted within a deep brain location or a cortical location for stimulation of brain tissue. The distal end of lead 701 may be implanted in a subcutaneous location for stimulation of a peripheral nerve or peripheral nerve fibers. Alternatively, the distal end of lead 701 positioned within the epidural space of a patient. Although some embodiments are adapted for stimulation of neural tissue of the patient, other embodiments may stimulate any suitable tissue of a patient (such as cardiac tissue). An "extension" lead (not shown) may be utilized as an intermediate connector if deemed appropriate by the physician.

Electrodes 705 include multiple segmented electrodes. The use of segmented electrodes permits the clinician to more precisely control the electrical field generated by the stimulation pulses and, hence, to more precisely control the stimulation effect in surrounding tissue. Electrodes 705 may also include one or more ring electrodes and/or a tip electrode. Any of the electrode assemblies and segmented electrodes discussed herein can be used for the fabrication of electrodes 705. Electrodes 705 may be utilized to electrically stimulate any suitable tissue within the body including, but not limited to, brain tissue, tissue of the spinal cord, peripheral nerves or peripheral nerve fibers, digestive tissue, cardiac tissue, etc. Electrodes 705 may also be additionally or alternatively utilized to sense electrical potentials in any suitable tissue within a patient's body.

Pulse generator 720 preferably wirelessly communicates with programmer device 750. Programmer device 750 enables a clinician to control the pulse generating operations of pulse generator 720. The clinician can select electrode combinations, pulse amplitude, pulse width, frequency parameters, and/or the like using the user interface of programmer device 750. The parameters can be defined in terms of "stim sets," "stimulation programs," (which are known in the art) or any other suitable format. Programmer device 750 responds by communicating the parameters to pulse generator 720 and pulse generator 720 modifies its operations to generate stimulation pulses according to the communicated parameters.

Figure 8:
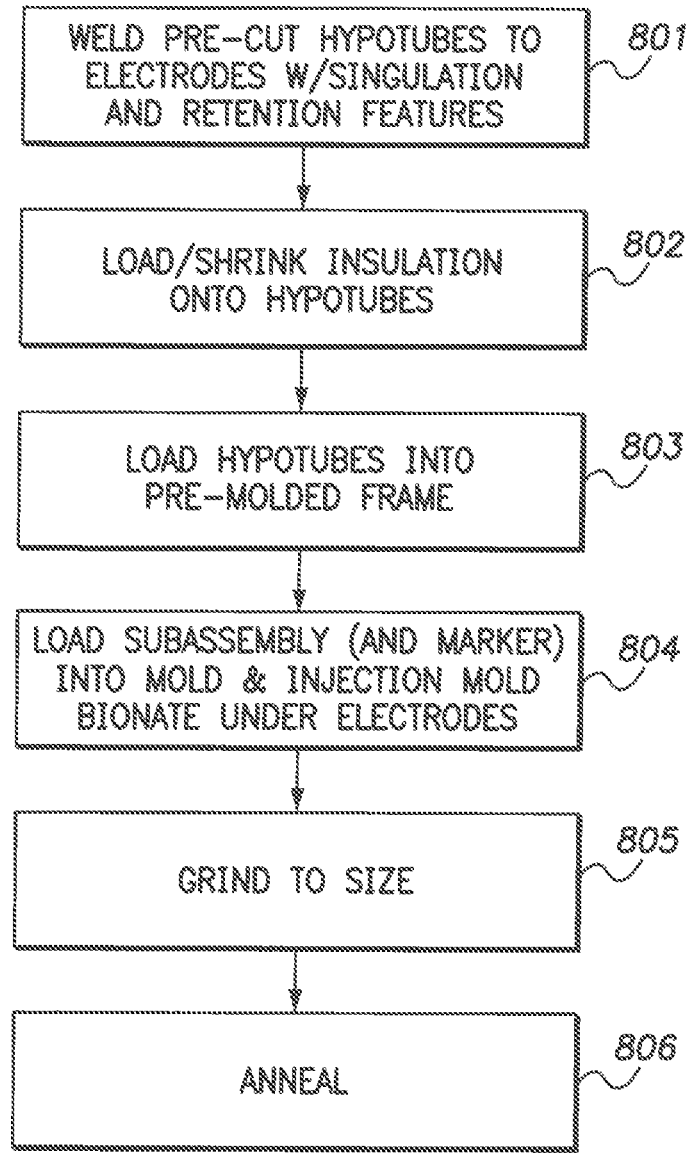
FIG. 8 depicts a flowchart of operations for fabrication of a stimulation end component according to one representative embodiment.

FIG. 8 depicts a flowchart of operations for fabrication of a stimulation end component according to one representative embodiment. In 801, pre-cut hypotubes are welded to electrodes that include singulation (e.g., grooves) and retention features (step-down regions). In some embodiments, the hypotubes are coated with insulative material before being welded to the electrodes. In one embodiment, a suitable thin coat (e.g., approximately 12 μm) of parylene is provided over each hypotube and the coated hypotubes are welded to the electrodes. The thin coating of parylene permits electrical isolation to be maintained between the various conductive components. The thin coating of parylene prevents shorting between respective hypotubes and other electrically conductive components. Further, it is has been determined by the present inventors that the thin coating of parylene does not affect the integrity of the subsequently created weld points between the hypotubes and other conductive components. In certain embodiments, the rings/electrode components may be additionally or alternatively coated with a thin layer of insulative material (e.g., parylene).

In some embodiments, multiple weld operations are provided for each hypotube. In one embodiment, a first weld is provided for each hypotube at the proximal end of its ring component and a second weld is provided for each hypotube at the distal end of its ring component. The first and second welds may improve the integrity of the connection between the hypotubes and the ring components. Pushing and pulling of the hypotubes may occur by the injection of insulative material during the molding process. This arrangement may cause the forces applied by the injection process to be placed on the first weld while maintaining the mechanical and electrical integrity of the second weld.

In 802, operations to load and shrink insulation onto hypotubes are performed. In 803, hypotubes are loaded into pre-molded frame component. The frame component may comprise an annular structure with multiple lumens to accommodate each hypotube. In 804, the subassembly and marker are loaded into a suitable mold and injection molding operations are performed to provide BIONATE™ or other suitable insulative material under the electrodes. After molding, the assembly is subjected to grinding to obtain the intended outer diameter size (805). In 806, annealing occurs. The terminal end component may be fabricated in a substantially similar manner.

Figure 9:
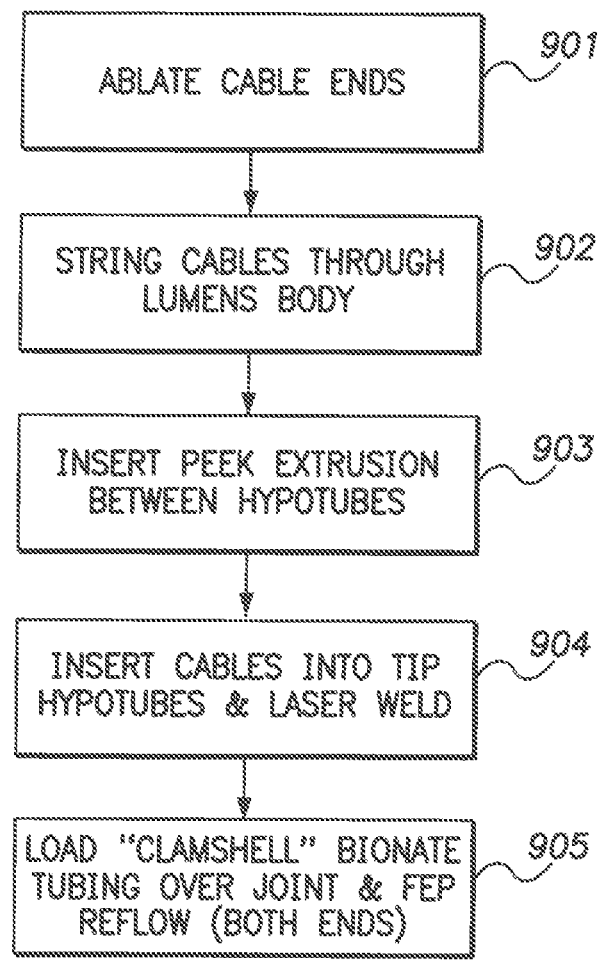
FIG. 9 depicts a flowchart for operations for joining a stimulation end component to a lead body component according to one representative embodiment.

FIG. 9 depicts a flowchart for operations for joining a stimulation end component to a lead body component according to one representative embodiment. In 901, conductor cable ends are ablated to expose conductive material from insulative sheaths about the conductors. In one embodiment, one or more of the conductors are coated with a suitable dye material or other colorant to facilitate identification of a specific channel in the finished stimulation tip component). In 902, the cables are strung through lumens of a lead body. In 903, a PEEK or other extrusion or molded component (see e.g., component 650 in FIG. 6) is inserted between the hypotubes to hold the hypotubes in place. In 904, cables are inserted into the hypotubes and laser welded. In 905, a "clamshell" of BIONATE™ (thermoplastic polycarbonate urethane) material or other reflowable insulative material is loaded over the joint between the components and reflow operations are performed. The reflow operations may include providing a FEP shrink wrap and applying sufficient heat as is known in the art of lead fabrication. The terminal end component may be joined to the lead body component in a substantially similar manner.

Figure 10:
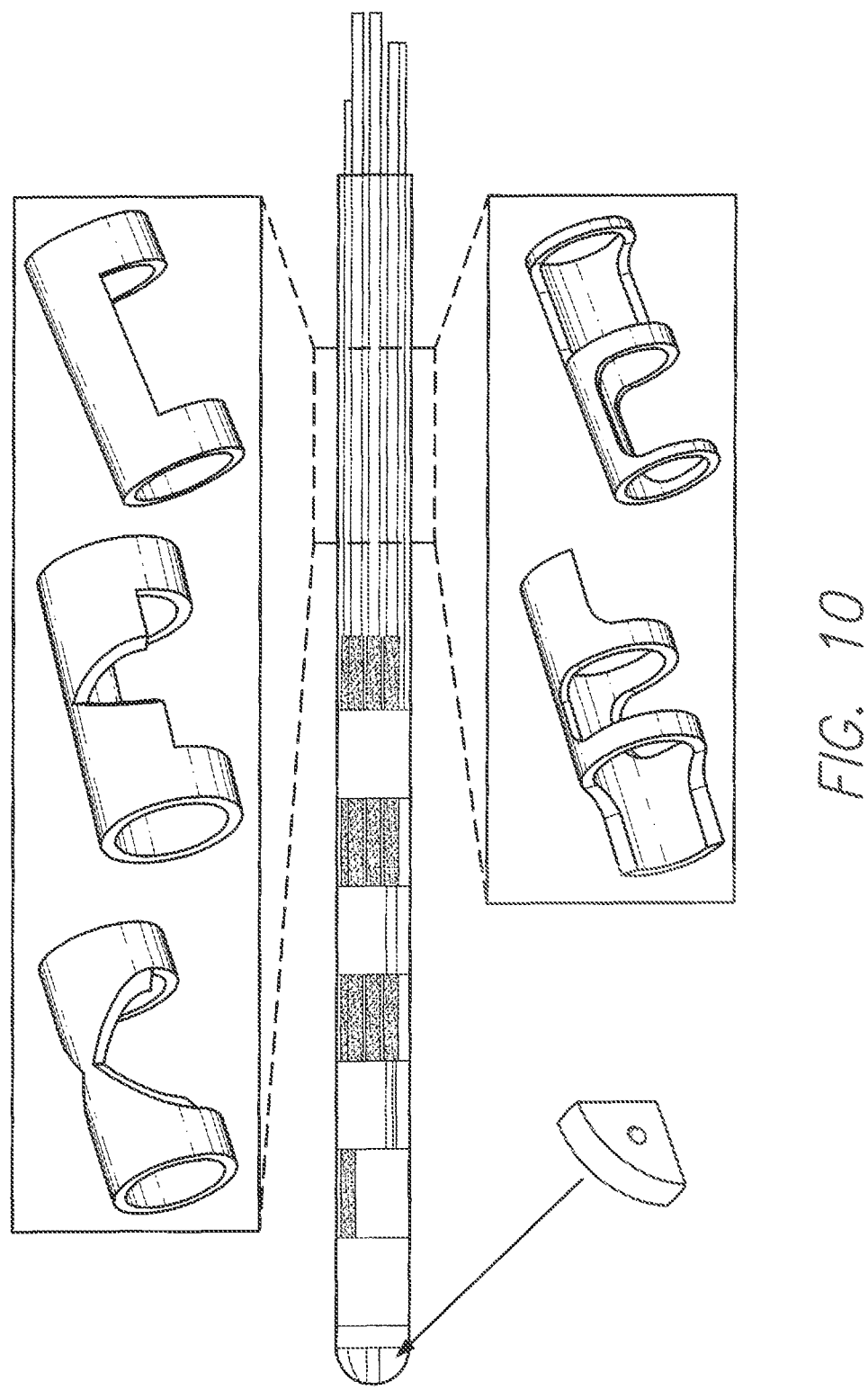
FIG. 10 depicts a plurality of different marker designs that permit the orientation of a stimulation lead with segmented electrodes to be determined post-implant.
Figure 12:
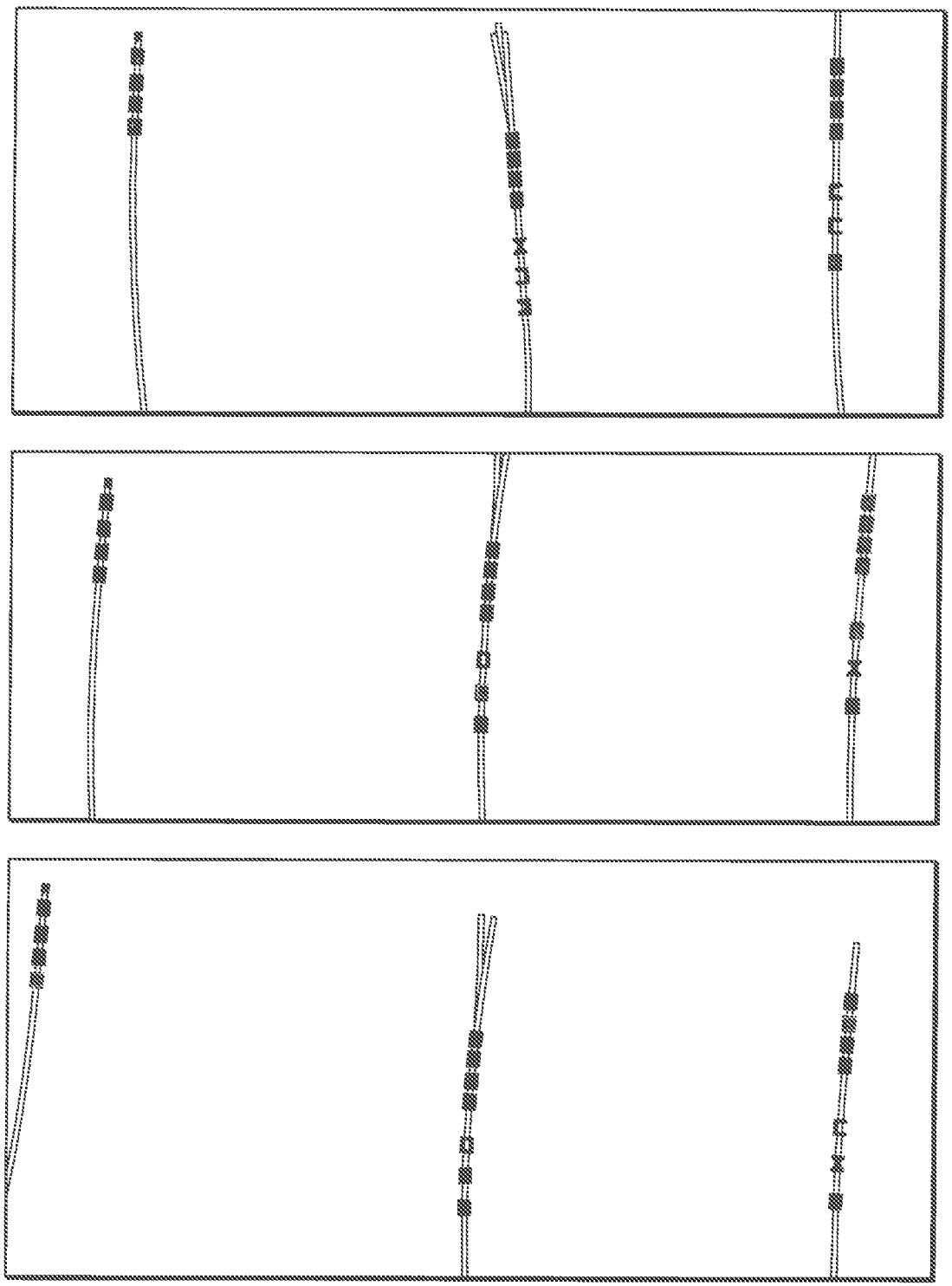
FIG. 12 depicts further images of segmented leads with markers according to some representative embodiments.

FIG. 10 depicts a plurality of different marker designs that permit the orientation of a stimulation lead with segmented electrodes to be determined post-implant. One marker may be provided at a distal or tip of the stimulation lead. Additionally or alternatively, another marker may be provided proximal to the electrodes of the stimulation lead about the outer surface of the lead body. FIG. 11 depicts the orientation of a lead with segmented electrodes and an orientation marker according to one representative embodiment matched against corresponding images of the lead. FIG. 12 depicts further images of segmented leads with markers according to some representative embodiments.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

The invention claimed is:

1. A method for fabricating a neurostimulation stimulation lead comprising:
   providing a plurality of ring components and hypotubes in a mold;
   molding the plurality of ring components and the hypotubes to form a stimulation tip component for the stimulation lead; and
   forming segmented electrodes from the ring components after performing the molding,
      wherein the plurality of hypotubes comprise different lengths for the corresponding hypotubes such that multiple ones of the plurality of hypotubes extend different lengths after the molding is performed to facilitate subsequent connection of the hypotubes to conductor wires of a lead body in a correct order.

2. The method of claim 1 wherein the plurality of hypotubes extend from the annular frame structure after the molding is performed.

3. The method of claim 1 wherein the molding fills interstitial spaces between the plurality of ring components and hypotubes with insulative material.

4. The method of claim 1 further comprising, prior to the molding, placing an annular frame with multiple lumens over proximal ends of the plurality of hypotubes to position a portion of each hypotube within a respective lumen of the annular frame.

5. The method of claim 1 wherein an insulative coating is disposed on each hypotube of the plurality of hypotubes.

6. The method of claim 5 wherein the insulative coating on each hypotube is one or more respective polyxylylene polymers.

7. The method of claim 1 wherein an insulative coating is disposed on an inner diameter of the segmented electrodes.

8. The method of claim 7 further comprising: welding conductor wires of a lead body to each hypotube coated with the one or more polyxylylene polymers.

9. The method of claim 1 further comprising: joining a lead body to the stimulation tip.

10. The method of claim 9 wherein the joining comprises: connecting a plurality of wires of the lead body to the hypotubes.

11. The method of claim 10 further comprising: placing a clam-shell shaped component of reflowable insulative material over the connection region between the plurality of wires and the hypotubes; and reflowing the material of the clam-shell component.

12. The method of claim 1 wherein each ring component comprises a step-down region that is secured underneath an outer surface of insulative material of the stimulation tip.

13. The method of claim 12 wherein the step-down region comprises a roughened surface.

14. The method of claim 13 further comprising: bead blasting the step-down region of each ring component to roughen the surface of the step-down region.

15. The method of claim 1 further comprising: twisting a lead body for the stimulation lead from a first configuration with linearly arranged conductor wires to obtain a second configuration with helically arranged conductor wires.

16. The method of claim 15 further comprising: heat setting the lead body to retain the second configuration with helically arranged conductor wires.

17. The method of claim 1 further comprising: applying a first weld and a second weld to attach each hypotube to a corresponding ring component.

* * * * *